United States Patent [19]

Obayashi et al.

[11] Patent Number: 4,732,968

[45] Date of Patent: Mar. 22, 1988

[54] PROCESS FOR GRANULATING A WATER-ABSORBENT RESIN EMPLOYING (A) WATER (B) INORGANIC POWDER & (C) SURFACTANT IN AN INERT SOLVENT

[75] Inventors: Shigeji Obayashi, Akashi; Morio Nakamura, Kakogawa, all of Japan; Takushi Yamamoto; Hitoshi Tanaka; Yuji Sakamoto; Yasuhiro Shimada, all of Himeji, Japan

[73] Assignee: Seitetsu Kagaku Co., Ltd., Hyogo, Japan

[21] Appl. No.: 937,284

[22] Filed: Dec. 3, 1986

[30] Foreign Application Priority Data

Dec. 4, 1985 [JP] Japan .................. 60-273682

[51] Int. Cl.$^4$ .................. C08J 3/12; C08K 3/44
[52] U.S. Cl. .................. 528/490; 524/37; 524/42; 524/43; 524/44; 524/493; 524/503; 524/504; 528/499; 528/501; 528/503
[58] Field of Search .................. 524/493, 37, 504, 503, 524/42, 43, 44; 528/490, 499, 501, 503

[56] References Cited

U.S. PATENT DOCUMENTS

| | | | |
|---|---|---|---|
| 4,093,776 | 6/1978 | Aoki et al. | 526/240 |
| 4,320,207 | 3/1982 | Watanabe et al. | 525/177 |
| 4,340,706 | 7/1982 | Obayashi et al. | 526/216 |
| 4,360,651 | 11/1982 | Dinbergs | 526/88 |
| 4,410,673 | 10/1983 | Schulz et al. | 526/202 |
| 4,435,523 | 3/1984 | Dinbergs | 526/209 |
| 4,446,261 | 5/1984 | Yamasaki et al. | 524/37 |
| 4,459,396 | 7/1984 | Yamasaki et al. | 526/306 |
| 4,507,438 | 3/1985 | Obayashi et al. | 525/119 |
| 4,541,871 | 9/1985 | Obayashi et al. | 525/123 |
| 4,663,383 | 5/1987 | Lowe et al. | 528/490 |

*Primary Examiner*—Herbert J. Lilling
*Attorney, Agent, or Firm*—Pollock, Vande Sande & Priddy

[57] ABSTRACT

A water-absorbent resin having an appropriate particle size and a narrow particle size distribution can be obtained by adding a powdered inorganic material in a proportion of 0.000005–0.2 part by weight to 1 part by weight of a water-absorbent resin containing therein a carboxylate as a component of the polymer with agitation in an inert solvent in the presence of 0.1–5.0 parts by weight of water and 0.005–0.2 part by weight of a surfactant and then removing water and the inert solvent by distillation.

11 Claims, No Drawings

PROCESS FOR GRANULATING A WATER-ABSORBENT RESIN EMPLOYING (A) WATER (B) INORGANIC POWDER & (C) SURFACTANT IN AN INERT SOLVENT

This invention relates to a process for granulating a water-absorbent resin, in particular a process for preparing a water-absorbent resin having an appropriate particle diameter and a narrow particle size distribution.

Recently, water-absorbent resins have been used in the field of sanitation as menstrual articles, diapers, disposable house-cloths and the like and in the field of agriculture and horticulture as water retentive materials, soil conditioners and the like. Further, they are useful in other various fields such as coagulation of sludges, prevention of dew condensation on construction materials, dehydration of oils and the like.

Water-absorbent resins have extensively been used particularly for sanitary products such as menstrual articles, diapers and the like.

As such water-absorbent resins, there are known crosslinked acrylic acid salt polymers, saponification products of crosslinked acrylic acid ester-vinyl acetate copolymers, crosslinked starch-acrylic acid salt graft copolymers, saponification products of crosslinked starch-acrylonitrile graft copolymers, crosslinked polyvinyl alcohols grafted with maleic anhydride, crosslinked polyethylene oxides and the like.

These water-absorbent resins are generally duced by synthesizing polymers by such a process as inverse suspension polymerization, inverse emulsion polymerization, aqueous solution polymerization or reactions in organic solvents and drying the polymers as such or subjecting the polymers after drying to grinding step, if necessary.

However, when a water-absorbent resin was produced by such a process, there was usually obtained a product having a wide range of particle size distribution and containing finely divided particles to a considerable extent.

When a powdery water-absorbent resin is used in the field of sanitation, it is frequently used by mixing with a ground pulp, spreading uniformly on a ground pulp layer or inserting between water-absorbent papers. In using a water-absorbent resin which consists of finely divided particles or contains a large amount of finely divided particles, it is hard to handle because it tends to cause bridging during transfer or feeding, and furthermore environment is sometimes deteriorated to a very inferior level because of rising of dust, which may cause the pollution or trouble of installations. Further, finely divided particles tend to drop off from sanitation products.

When such a water-absorbent resin is used as a water-retentive material for agriculture and horticulture, it may be attached to machines or may form ununiform mixtures in mixing thereof with soil or sand.

The present inventors have conducted earnest researches for excluding the aforementioned defects in the conventional techniques and for seeking a process for preparing stably and easily a water-absorbent resin which has particle sizes depending on its applications and a narrow particle size distribution and will not produce dust. As a result thereof, they have found that a water-absorbent resin having appropriate particle sizes and a narrow particle size distribution and excluding finely divided particles having a particle size of 100$\mu$ or less can be obtained by adding a powdered inorganic material in a proportion of 0.000005–0.2 part by weight to 1 part by weight of a water-absorbent resin containing therein a carboxylate as a component of the polymer with agitation in an inert solvent in the presence of 0.1–5.0 parts by weight of water and 0.005–0.2 part by weight of a surfactant and then removing water and the inert solvent by distillation. Thus, they have accomplished the present invention.

The water-absorbent resin containing a carboxylate as a constituent of the polymer according to this invention includes crosslinked acrylic acid salt polymers, saponification products of crosslinked acrylic acid ester-vinyl acetate copolymers, crosslinked starch-acrylic acid salt graft copolymers, saponification products of crosslinked starch-acrylonitrile graft copolymers, crosslinked polyvinyl alcohols grafted with maleic anhydride and the like. These resins are preferably used in this invention. It is needless to say that a copolymer having as a main component thereof an acrylic acid salt such as crosslinked acrylic acid salt-acrylamide copolymers, crosslinked acrylic acid salt-2-acrylamide-2-methylpropane sulfonic acid salt copolymers or the like may be used in this invention. The embodiments of this invention are now explained in detail. The water-absorbent resin containing a carboxylate can be prepared by any one of the processes which are disclosed in Japanese Patent Publication No. 25045/85, Japanese Patent Application No. 210198/84, Japanese Patent Application Kokai (Laid-Open) Nos. 158210/82 and 21405/82, Japanese Patent Publication No. 46199/78, Japanese Patent Application Kokai (Laid-Open) Nos. 71907/83 and 84304/80 and the like.

Typical preparation examples of the water-absorbent resin are illustrated below.

PREPARATION EXAMPLE 1

A process which comprises suspending an aqueous solution of an $\alpha, \beta$-unsaturated carboxylic acid and an alkali metal salt thereof in a petroleum hydrocarbon solvent containing a saccharose fatty acid ester in the presence or absence of a crosslinking agent and subjecting the suspension to polymerization in the presence of a radical polymerization initiator.

PREPARATION EXAMPLE 2

A process which comprises suspending an aqueous solution of acrylic acid and an alkali salt of acrylic acid in an alicyclic or aliphatic hydrocarbon solvent containing a surface active agent having an HLB value of 8–12 and subjecting the suspension to polymerization in the presence of a water soluble radical polymerization initiator.

PREPARATION EXAMPLE 3

A process which comprises suspending an aqueous solution of a monomer in a hydrophobic liquid inert to the polymerization by using as a protective colloid a reaction product obtained by grafting 1–20% by weight of an $\alpha, \beta$-unsaturated polyvalent carboxylic acid or an anhydride thereof to a monoolefin polymer having a molecular weight of 750–10,000 or a product obtained by oxidizing said monoolefin polymer to a final acid value of 10–100, and subjecting the suspension to polymerization in the presence of a water soluble radical polymerization initiator.

PREPARATION EXAMPLE 4

A process which comprises dispersing or suspending an aqueous solution of a water soluble ethylenic unsaturated monomer, the concentration of said solution being 40% by weight to the saturation concentration, in a hydrocarbon or a halogenated aromatic hydrocarbon by using a cellulose ester or cellulose ether which is oil soluble at the polymerization temperature as a protective colloid, and subjecting the mixture to polymerization using a persulfate as a polymerization initiator.

PREPARATION EXAMPLE 5

A process for preparing a polymer which comprises polymerizing (A) at least one of starch and cellulose, (B) at least one of monomers having a double bond being capable of causing addition polymerization which are water soluble or become water soluble by hydrolysis and (C) a crosslinking agent as the essential constituents, and subjecting the polymerization product to hydrolysis, if necessary.

PREPARATION EXAMPLE 6

A process for preparing a water-absorbent resin which comprises adding a polymerization initiator to a warmed aqueous solution containing potassium acrylate and a water miscible or water soluble divinyl compound, the concentration of said monomers being in the range of 55–80% by weight, subjecting the mixture to polymerization without external heating, and vaporizing the water.

The water-absorbent resin used in this invention may be prepared by any producing process without limitation to those mentioned above.

According to this invention, when these water-absorbent resins are granulated, they are allowed to contain a certain amount of water. However, the effects of this invention vary greatly depending upon the proportion of water to be contained. Thus, in this invention, the amount of water to be contained should be varied within the range of 0.1–5.0 parts by weight to 1 part by weight of water-absorbent resins.

If the amount of water is 0.1 part by weight or less, no granulation is obtained or the effect of granulation, even if obtained, is poor. On the other hand, if the amount of water is 5.0 parts by weight or more, bulk materials are obtained in place of granules, or the granules, even if obtained, are unfavorably coarse.

From such relationships, more preferable results are obtained in the case of particularly 0.2–3.0 parts by weight of the amount of water. Further, it is also possible to obtain particles having no finely divided particles of 100μ or less and having appropriate particle sizes, the distribution of which is narrow, by changing the amount of water within the range mentioned above.

As the surface active agent used in this invention, there may be cited sorbitan fatty acid esters or sorbitan fatty acid ester ethers having an HLB of 8–12 such as sorbitan monolaurylate or oxyethylene sorbitan monostearate ether; saccharose fatty acid esters having an HLB of 2–16; cellulose esters or cellulose ethers; low molecular weight monoolefin polymers or low molecular weight diolefin polymers grafted with maleic anhydride; monoolefin polymers having an acid value of 10–100 or the like.

However, if the process according to this invention is carried out with a sorbitan fatty acid ester having a low HLB value such as sorbitan monostearate (HLB=4.7) among sorbitan fatty acid esters, there are obtained the only granules that will be finely divided by applying a little force. Thus, such a case does not attain the object of this invention.

When the amount of the surface active agent used is 0.005 part by weight or less to 1 part by weight of a water-absorbent resin, it is difficult to obtain products having an appropriate particle size and coarse particles or bulk products are obtained. Thus, the case is not preferred. When the amount of the surface active agent is 0.2 part by weight or more, it contributes little to granulation. Further, it gives bad influences on the performances of a water-abosrbent resin and such case is not economical. Thus, the case is not preferred either.

The inert solvent used in this invention may be any one that will not give bad influences on the polymer and its constituents. Particularly, when a petroleum oil solvent or a lower alcohol is used, a preferable result is obtained.

The petroleum oil solvent includes aliphatic hydrocarbons, alicyclic hydrocarbons and aromatic hydrocarbons. As the aliphatic hydrocarbons, there are cited normal pentane, normal hexane, normal heptane, ligroin and the like. As the alicyclic hydrocarbons, there are cited cyclopentane, methylcyclopentane, cyclohexane, methylcyclohexane and the like. As the aromatic hydrocarbons, there are cited benzene, toluene, xylene and the like.

As the lower alcohols, there are cited methanol, ethanol, isopropanol and the like. Particularly, normal hexane, normal heptane, cyclohexane, toluene, xylene and methanol are industrially stable in their qualities. Furthermore, they are easily available and inexpensive, so that they can be used advantageously.

When the water-absorbent resin and the inert solvent are used generally in a ratio of 1–100 parts by weight, preferably 2–50 parts by weight of the inert solvent to 1 part by weight of the water-absorbent resin, a preferred result is obtained. The less the amount of the inert solvent, the better the volumetric efficiency. However, the dispersion of the water-absorbent resin in a water-containing state is deteriorated, and a bulk product is often produced upon addition of a powdery inorganic material. On the other hand, when the amount of the inert solvent is too much, said water-absorbent resin is easily dispersed and granulation is carried out homogeneously, so that the range of the particle size distribution becomes narrow. However, the volumetric efficiency is lowered. Thus, it is preferred to conduct granulation within the aforementioned range of the ratio.

As the powdery inorganic materials which can be used in this invention, there are mentioned, for example, silicon dioxide, aluminum oxide, titanium dioxide, calcium phosphate, calcium carbonate, talc, magnesium phosphate, calcium sulfate, diatomaceous earth, bentonite, zeolite, other metal oxides and the like. In particular, silicon dioxide, aluminum oxide and titanium dioxide are preferred. There are preferably used these powdery inorganic materials having a particle size of generally 200μ or less, particularly 100μ or less.

If the amount of the powdery inorganic material added is used in a proportion of generally 0.000005–0.2 part by weight, preferably 0.000005–0.1 part by weight to the water-absorbent resin, a preferable result is obtained. Generally when the amount of the powdery inorganic material added is less than 0.000005 part by weight, no effect of addition appears. When it exceeds 0.2 part by weight, the performance of the water-absorbency is unfavorably deteriorated.

Particles having an appropriate particle size, the distribution of which is in a narrow range, can be obtained by changing the amount to be added within the aforementioned ranges. In order to obtain stable granules having a narrow particle size distribution, it is necessary to use an apparatus wherein homogeneous dispersion can be accomplished for the entire suspension.

The embodiments of this invention include various processes. For example, a water-absorbent resin having a suitable particle size can be obtained by dispersing a water-absorbent resin in an inert solvent containing a surface active agent, adding water with agitation to the dispersion for uniform absorption of water into the water-absorbent resin, adding a powdery inorganic material therein and then evaporating water and said solvent in a usual manner, or by conducting polymerization reaction for getting a water-absorbent resin by use of the aforementioned inert solvent, controlling, if necessary, the ratio of the three, that is, the water-absorbent resin, water and the surface active agent in the polymerization liquid obtained from said reaction step, adding a powdery inorganic material to the mixture, and finally evaporating water and the solvent.

In the conventional processes for producing water-absorbent resins, final products contained finely divided particles, especially those having a particle size of $100\mu$ or less in a considerable proportion, and products having a wide particle size distribution were usually obtained.

When the granulation process according to this invention is used, it is possible to obtain a water-absorbent resin which contains none of the finely divided particles and has an appropriate particle size depending on its application and a narrow particle size distribution. Thus, no dust will be caused on transfer or packaging operations, and it is possible to prevent the deterioration of working environment and the contamination or trouble of apparatuses.

The water-absorbent resin according to this invention, when used as sanitary products or agricultural or horticultural products, does not drop off fine powders. Moreover, a water-absorbent resin having a suitable particle size depending on its applications can be obtained according to this invention, so that the spreadability, mixing property, water-retentive property and the like of the resin can be remarkably improved according to this invention.

This invention will be actually illustrated by the following Examples and Comparative Examples.

COMPARATIVE EXAMPLE 1

In a 500 ml four-neck round bottom flask equipped with a stirrer, a reflux condenser, a dropping funnel and a nitrogen gas introducing tube was charged 280 ml of n-heptane, and then 0.75 g of saccharose di- and tri-stearate having an HLB value of 3 was dispersed in the solvent. Oxygen dissolved in the dispersion was purged by blowing nitrogen gas, and the temperature of the mixture was raised up to 50° C. to dissolve with agitation the saccharose di- and tri-stearate. The resultant solution was then cooled to 30° C.

In a 200 ml Erlenmeyer flask was separately placed 37.5 g of 80% by weight aqueous acrylic acid solution, and subsequently 75 molar % neutralization was carried out with external ice-cooling by dropping 49.3g of 25.4% by weight aqueous sodium hydroxide solution, and then 0.045g of potassium persulfate was added and dissolved therein.

The partially neutralized aqueous acrylic acid salt solution was added in the four-heck flask to disperse it, and the system was sufficiently purged with nitrogen again, and then the temperature was raised to maintain the temperature of the bath at 55-65° C. The polymerization reaction was conducted for 1 hour to obtain the polymerization liquid product of a water-absorbent resin. Water and n-heptane were removed by distillation, and the residue was dried to obtain 41.0 g of polymer beads having a particle size of 150-400$\mu$.

EXAMPLES 1-11

A powdery inorganic material was added with stirring to the polymerization liquid product mentioned above and those stated hereinafter which contain water-absorbent resins, water, inert solvents and surface active agents. The water and the inert solvents were removed by distillation and drying was conducted to obtain granulated water-absorbent resins. The results are shown in Table 1 below. The amounts and particle sizes of the water-abosrbent resins obtained in the Comparative Example 1 mentioned above and Comparative Examples 2, 3, and 4 stated hereinafter are also shown in the right column of Table 1 for comparison.

TABLE 1

| Example No. | Polymerization liquid product | Powdery inorganic material Name of the material | Powdery inorganic material Amount added (g) | Water-absorbent resin Amount produced (g) | Water-absorbent resin Particle size ($\mu$) | Water-absorbent resin in Comparative Examples Amount produced (g) | Water-absorbent resin in Comparative Examples Particle size ($\mu$) |
|---|---|---|---|---|---|---|---|
| 1 | Liquid product obtained under the same conditions as in Comparative Example 1 | SiO$_2$ (TOKUSIL P) | 0.75 | 42.0 | 400–900 | 41.0 | 150–400 |
| 2 | Liquid product obtained under the same conditions as in Comparative Example 1 | Al$_2$O$_3$ (Aluminum Oxide C) | 0.75 | 42.5 | 350–1200 | 41.0 | 150–400 |
| 3 | Liquid product obtained under the same conditions as in Comparative | TiO$_2$ (Titanium Oxide P-25) | 0.75 | 42.3 | 300–900 | 41.0 | 150–400 |

TABLE 1-continued

| Example No. | Polymerization liquid product | Powdery inorganic material Name of the material | Amount added (g) | Water-absorbent resin Amount produced (g) | Particle size (μ) | Water-absorbent resin in Comparative Examples Amount produced (g) | Particle size (μ) |
|---|---|---|---|---|---|---|---|
| 4 | Example 1 Liquid product obtained under the same conditions as in Comparative Example 1 | SiO$_2$ (Aerosil 200) | 0.75 | 42.5 | 400–1000 | 41.0 | 150–400 |
| 5 | Liquid product obtained under the same conditions as in Comparative Example 1 | SiO$_2$ (TOKUSIL P) | 0.0037 | 41.8 | 250–600 | 41.0 | 150–400 |
| 6 | Product which was obtained by removing 22 g of water from the polymerization liquid obtained under the same conditions as in Comparative Example 1 | SiO$_2$ (TOKUSIL P) | 0.75 | 41.5 | 300–800 | 41.0 | 150–400 |
| 7 | Product which was obtained by adding 23.8 g of water to the polymerization liquid obtained under the same conditions as in Comparative Example 1 | SiO$_2$ (TOKUSIL P) | 0.75 | 42.3 | 700–1500 | 41.0 | 150–400 |
| 8 | Liquid product obtained under the same conditions as in Comparative Example 2 | SiO$_2$ (TOKUSIL NR) | 0.24 | 49.5 | 300–900 | 48.0 | 50–350 |
| 9 | Liquid product obtained under the same conditions as in Comparative Example 2 | SiO$_2$ (TOKUSIL P) | 3.4 | 52.0 | 250–840 | 48.0 | 50–350 |
| 10 | Liquid product obtained under the same conditions as in Comparative Example 3 | Al$_2$O$_3$ (Aluminum Oxide C) | 0.56 | 41.6 | 300–1000 | 40.0 | 50–350 |
| 11 | Liquid product obtained under the same conditions as in Comparative Example 4 | SiO$_2$ (Aerosil R 972) | 0.56 | 41.8 | 300–1000 | 40.5 | 50–350 |

Note
1: TOKUSIL P: Tradename, manufactured by Tokuyama Soda Co., Ltd.
2: TOKUSIL NR: Tradename, manufactured by Tokuyama Soda Co., Ltd.
3: Aluminum Oxide C: Tradename, manufactured by Nippon Aerosil Co., Ltd.
4: Aerosil R 972: Tradename, manufactured by Nippon Aerosil Co., Ltd.
5: Titanium Oxide P25: Tradename, manufactured by Nippon Aersil Co., Ltd.
6: Aerosil 200: Tradename, manufactured by Nippon Aersil Co., Ltd.

COMPARATIVE EXAMPLE 2

In the same 500 ml four-neck round flask as used in Comparative Example 1 was charged 213 g of cyclohexane, and then 0.8 g of sorbitane monolaurate having an HLB value of 8.6 was added and dispersed in the solvent. Oxygen dissolved in the dispersion was purged by blowing nitrogen gas, and the sorbitan monolaurate was dissolved with agitation at room temperature.

In a 200 ml Erlenmeyer flask was separately placed 39.1 g of acrylic acid having a purity of 99.8% by weight, and 80 molar % of the acrylic acid was neutralized with external ice-cooling by dropping 76.5 g of 22.6% by weight of aqueous sodium hydroxide solution, and then 0.13 g of potassium persulfate was added and dissolved therein.

The partially neutralized aqueous acrylic acid salt solution was added in the four-neck flask to disperse it, and the system was sufficiently purged with nitrogen again, and then the temperature was raised to maintain the temperature of the bath at 55–60° C. The polymerization reaction was conducted for 3 hours to obtain the polymerization liquid product of a water-absorbent resin. The water and the cyclohexane were removed by distillation, and the residue was dried to obtain 48.0 g of a dried polymer in the form of fine particles having a particle size of 50–350$\mu$.

COMPARATIVE EXAMPLE 3

In the same 500 ml four-neck round flask as used in Comparative Example 1 was charged 280 ml of nheptane and then 2.3 g of modified polyethylene wax (tradename: Hi-Wax 1105A, manufactured by Mitsui Petrochemical Industries, Ltd., molecular weight: 2700, density: 0.94, acid value: 30) was added and dispersed in the solvent. Oxygen dissolved in the dispersion was purged by blowing nitrogen gas, and the modified polyethylene wax was dissolved with agitation by raising the temperature up to 65° C.

In an Erlenmeyer flask was separately placed 37.5 g of 80% by weight aqueous acrylic acid solution and 75 molar % of neutralization was carried out with external ice-cooling by dropping 44.5 g of 28.1% by weight of aqueous sodium hydroxide solution, and then 0.045 g of potassium persulfate was added and dissolved therein.

The partially neutralized aqueous acrylic acid salt solution was added in the four-neck flask to disperse it, and the system was sufficiently purged with nitrogen again, and the temperature was raised to maintain the temperature of the bath at 60–65° C. The polymerization reaction was conducted for 1 hour to obtain the polymerization liquid product of a water-absorbent resin. The water and the n-heptane was removed by distillation, and the residue was dried to obtain 40 g of polymer beads having a particle size of 50–350$\mu$.

COMPARATIVE EXAMPLE 4

In the same 500 ml four-neck round flask as used in Comparative Example 1 was charged 280 ml of cyclohexane, and then 1.86 g of ethylcellulose (tradename: Ethylcellulose N-200, manufactured by Hercules) was added and dispersed in the solvent. Oxygen dissolved in the dispersion was purged by blowing nitrogen gas, and the ethylcellulose was dissolved by raising the temperature up to 75° C.

In an Erlenmeyer flask was separately placed 37.5 g of 80% by weight aqueous acrylic acid solution, and 75 molar % of neutralization was carried out with external ice-cooling by dropping 44.5 g of 28.1% by weight of aqueous sodium hydroxide solution and then 0.045 g of potassium persulfate was added and dissolved therein.

The partially neutralized aqueous acrylic acid salt solution was added in the four-neck flask to disperse it, and the system was again sufficiently purged with nitrogen, and then the temperature was raised to maintain the temperature of the bath at 60–65° C. The polymerization reaction was conducted for 1 hour to obtain the polymerization liquid product of a water-absorbent resin. The water and cyclohexane were removed by distillation, and the residue was dried to obtain 40.5 g of polymer beads having a particle size of 50–350$\mu$.

EXAMPLE 12

In a 500 ml four-neck round bottom flask equipped with a stirrer, a reflux condenser, a water-separator, a dropping funnel and a nitrogen gas introducing tube was charged 50 g of a commercial water-absorbent resin, crosslinked starch-acrylic acid salt graft polymer (tradename: SANWET IM-1000, manufactured by Sanyo Chemical Ind., Ltd.; particle size: 30–840$\mu$, water content: 9.0%), and then 300 ml of n-heptane and 2.5 g of sorbitan monolaurate were added, and 45.5 g of water was slowly added with agitation from the dropping funnel.

To the suspension was added 0.68 g of silica (tradename: TOKUSIL P. manufactured by Tokuyama Soda Co., Ltd.), and then the water and n-heptane were removed by distillation, and the residue was dried to obtain 53.5 g of granules having a particle size of 350–900$\mu$.

EXAMPLE 13

In the same apparatus as used in Example 12 was charged 50 g of a commercial water-absorbent resin, crosslinked acrylic acid salt polymer (tradename: Arasorb 720, manufactured by ARAKAWA KAGAKU; particle size: 50–900$\mu$, water content: 10%), and then 300 ml of n-heptane and 2.5 g of sorbitan monolaurate were added, and 20 g of water was slowly added with agitation from the dropping funnel. To the suspension was added 0.45 g of silica (tradename: TOKUSIL P, manufactured by Tokuyama Soda Co., Ltd.), and then the water and n-heptane were removed by distillation, and the residue was dried to obtain 53.0 g of granules having a particle size of 300–1000$\mu$.

EXAMPLE 14

In the same apparatus as used in Example 12 was charged 30 g of the water-absorbent resin (water content: 5.0%) obtained in Comparative Example 1, and then a liquid mixture of 60 g of methanol, 60 g of water and 1.7 g of sorbitane mcnolaurate was added and mixed well. To the suspension was added 0.25 g of silica (tradename: TOKUSIL P, manufactured by Tokuyama Soda Co., Ltd.). The water and methanol were subsequently removed by distillation, and the residue was dried to obtain 30.5 g of granules having a particle size of 500–1000$\mu$.

EXAMPLE 15

In the same apparatus as used in Example 12 was charged 50 g of a commercially available water-absorbent resin, crosslinked polyvinyl alcohol grafted with maleic anhydride (Tradename: KI Gel, manufactured by Kuraray Co., Ltd., particle size: 30–1000$\mu$, water content: 8.0%), and then 300 ml of cyclohexane and 1.0 g of sorbitan monolaurate were added, and 46 g of water was slowly added with agitation from the dropping funnel. To the suspension was added 0.23 g of silica (tradename: Aerosil 380, manufactured by Nippon Aerosil Co., Ltd.). The water and cyclohexane were subsequently removed by distillation, and the residue was dried to obtain 51.5 g of granules having a particle size of 500–1400$\mu$.

EXAMPLE 16

In the same apparatus as used in Example 12 was charged 50 g of a commercially available water-absorbent resin, saponification product of crosslinked acrylic acid ester-vinyl acetate copolymer (Tradename: Sumikagel S-50, manufactured by Sumitomo Chemical Co., Ltd., particle size: 80–400μ, water content: 5.0%), and then 300 ml of cyclohexane and 1.0 g of sorbitan monolaurate were added, and 47.5 g of water was slowly added with agitation from the dropping funnel. To the suspension was added 0.5 g of silica (tradename: Aerosil 130, manufactured by Nippon Aerosil Co., Ltd.). The water and cyclohexane were subsequently removed by distillation, and the residue was dried to obtain 52.5 g of granules having a particle size of 300–800μ.

COMPARATIVE EXAMPLE 5

Com

In the same apparatus as used in Example 12 was charged 30 g of the water-absorbent resin, obtained in Comparative Example 2 (water content: 5.0%), and then 280 ml of n-heptane was added and the mixture was mixed well. Then, 0.75 g of silica (tradename: TOKUSIL P, manufactured by Tokuyama Soda Co., Ltd.) was added therein with agitation. The n-heptane was subsequently removed by distillation, and the residue was dried to obtain 29.5 g of a particulate polymer having the same particle size as the original one of 50–350μ.

COMPARATIVE EXAMPLE 6

In the same apparatus as used in Example 12 except the volume of 2 liters was charged 50 g of a commercially available water-absorbent resin (tradename: AQUALIC CA, manufactured by Nippon Shokubai Kagaku Kogyo Co., Ltd., water content: 9.0%), and then 1000 ml of n-heptane and 2.5 g of sorbitan monolaurate were added and 314 g of water was slowly added with agitation from the dropping funnel. Then, 0.68 g of silica (tradename: TOKUSIL P, manufactured by Tokuyama Soda Co., Ltd.) was added to the suspension. The water and n-heptane were subsequently removed by distillation, and the residue was dried to obtain only 10 g of granules with the rest being bulk.

COMPARATIVE EXAMPLE 7

Experiment was conducted in the same manner as in Example 12 except that no sorbitan monolaurate was used. Most of the product was bulk with granules being obtained only in an amount of 5 g.

We claim:

1. A process for granulating a water-absorbent resin, characterized in that 0.000005–0.2 part by weight of a powdery inorganic material is added with agitation in an inert solvent in the presence of 0.1–5.0 parts by weight of water and 0.005–0.2 part by weight of a surface active agent to 1 part by weight of a water-absorbent resin containing a carboxylate as a constituent of the polymer, and the water and the inert solvent are removed by distillation.

2. A process according to claim 1, wherein said water-absorbent resin is one or more of resins selected from the group consisting of crosslinked acrylic acid salt polymers, saponification products of crosslinked acrylic acid ester-vinyl acetate copolymers, crosslinked starch-acrylic acid salt graft copolymers, saponification products of crosslinked starch-acrylonitrile graft copolymers and crosslinked polyvinyl alcohols grafted with maleic anhydride.

3. A process according to claim 1, wherein said surface active agent is one or more of surface active agents selected from the group consisting of sorbitan fatty acid esters or sorbitan fatty acid ester ethers having an HLB value of 8–12, saccharose fatty acid esters having an HLB value of 2–16, cellulose esters or cellulose ethers, low molecular weight monoolefin polymers or low molecular weight diolefin polymers grafted with maleic anhydride and monoolefin polymers having an acid value of 10–100.

4. A process according to claim 1, wherein the amount of the inert solvent used is in a proportion of 2–50 parts by weight to 1 part by weight of the water-absorbent resin.

5. A process according to claim 1, wherein said inert solvent is a petroleum oil solvent.

6. A process according to claim 5, wherein said petroleum oil solvent is n-heptane.

7. A process according to claim 1, wherein said inert solvent is a lower alcohol.

8. A process according to claim 7, wherein said lower alcohol is methanol.

9. A process according to claim 1, wherein a powdery inorganic material having a particle size of 100μ or less is used.

10. A process according to claim 1, wherein said powdery inorganic material is silicon dioxide.

11. The process of claim 1 wherein said water-absorbent resin is at least one crosslinked acrylic acid salt polymer; said surface active agent is saccharose fatty acid ester having an HLB value of 2–16, and said powdery inorganic material is silicon dioxide.

* * * * *